(12) United States Patent
Oses et al.

(10) Patent No.: US 6,890,895 B2
(45) Date of Patent: May 10, 2005

(54) FIBER-SOFTENING COMPOSITIONS CONTAINING NON-IONIC SURFACTANTS

(75) Inventors: Maria José Bermejo Oses, Babera del Valles (ES); Josep Vilaret Ferrer, Barbera del Valles (ES); Marisa Mumbru Tomas, Barbera del Valles (ES)

(73) Assignee: Kao Corporation S.A., Barbera del Valles (ES)

( * ) Notice: Subject to any disclaimer, the term of this patent is extended or adjusted under 35 U.S.C. 154(b) by 6 days.

(21) Appl. No.: 10/602,401

(22) Filed: Jun. 23, 2003

(65) Prior Publication Data

US 2004/0014626 A1 Jan. 22, 2004

Related U.S. Application Data

(63) Continuation of application No. PCT/ES01/00472, filed on Dec. 3, 2001.

(30) Foreign Application Priority Data

Dec. 22, 2000 (ES) ............................................... 0003082

(51) Int. Cl.$^7$ ............................ C11D 1/48; C11D 1/835
(52) U.S. Cl. ........................ 510/504; 510/522; 510/527
(58) Field of Search ................................ 510/504, 522, 510/527

(56) References Cited

U.S. PATENT DOCUMENTS 5,854,201 A    12/1998    Behler et al.

FOREIGN PATENT DOCUMENTS

| DE | 019715835 C1 | * 11/1998 |
| DE | 019743687 C1 | * 11/1998 |
| EP | 1136471 A1 | 9/2001 |
| WO | WO 96/12002 | 4/1996 |
| WO | WO 96/35661 | * 11/1996 |
| WO | WO 98/49132 | 11/1998 |
| WO | WO 00/58429 | 10/2000 |

* cited by examiner

*Primary Examiner*—John R. Hardee
(74) *Attorney, Agent, or Firm*—Scully, Scott Murphy & Presser

(57) ABSTRACT

A description is given of novel aqueous compositions that soften and condition textiles and other natural and synthetic fibres, which compositions contain surfactants of a non-ionic character and cationic surfactants or esterquats obtained from alkanolamine esters based on the esterification reaction of optionally alkoxylated alkanolamines with dicarboxylic acids and fatty alcohols which are optionally alkoxylated.

The mentioned cationic surfactants and esterquats improve the conditioning and softening efficiency of non-ionic surfactants on natural and synthetic fibres so that the softening compositions obtained exhibit a high degree of efficiency in the treatment of fibres, such as textiles, paper and hair, and also facilitate ironing in the case of textile fibres and combing in the case of natural fibres.

18 Claims, No Drawings

FIBER-SOFTENING COMPOSITIONS CONTAINING NON-IONIC SURFACTANTS

The present application is a Continuation of PCT application Ser. No. PCT/ES01/00472, dated Dec. 3, 2001.

DESCRIPTION

1. Technical Field

The present invention relates to novel aqueous softening and conditioning compositions for textiles and other natural and synthetic fibres, which compositions contain non-ionic surfactants having a softening character and cationic surfactants or esterquats obtained from alkanolamine esters based on the esterification reaction of optionally alkoxylated alkanolamines, dicarboxylic acids, and optionally alkoxylated fatty alcohols.

2. Prior Art

For some decades, extensive use has been made of cationic surfactants derived from amines as softening and conditioning agents for all types of natural and synthetic fibres, being applied in fields such as the treatment of textile fibres and paper, and products for hair hygiene.

For ecological reasons, owing to their higher biodegradability, it has been common practice for some years to use cationic amine derivatives in which the hydrophobic hydrocarbon chains are interrupted by functional groups of the ester type, the most commonly used being quatemised derivatives of polyalkanolamine esters, which are normally known as esterquats. Among these, one of the most commonly used types, owing to their lower cost, are esterquats derived from triethanolamine.

British patent GB-602048 describes oligomeric alkanolamine esters which are based on the esterification reaction of triethanolamine with dicarboxylic acids and fatty acids, and their quaternisation with methyl chloride or dimethyl sulphate and their use as softening agents for natural and synthetic fibres, and U.S. Pat. No. 4,719,382 and U.S. Pat. No. 4,237,016 describe the use of the esterquats described in the above-mentioned British patent, among many other types of cationic polymer, as additives for improving the softening efficiency of cationic surfactants that do not contain ester groups. In addition, patent application WO-A-9812293 describes the use of those same oligomeric esterquats as additives to be incorporated in the aqueous phase of softening compositions containing esterquats, for the purpose of improving the softening efficiency thereof.

German patent DE-C-19539846 describes the synthesis of esterquats derived from dicarboxylic acids, fatty acids and triethanolamine and the use thereof as hair conditioners, and patent DE-C-19715835 describes esterquats based on the reaction of methyldiethanolamine and mixtures of fatty acids and dicarboxylic acids, with subsequent ethoxylation and/or quaternisation.

Patent WO-A-9849132 describes the synthesis of esterquats derived from dicarboxylic acid/fatty acid/triethanolamine, within a selected specific range of ratios, and their use in textile-softening compositions.

Patent DE-C-19519876 describes esterquats based on the reaction of a trialkanolamine with mixtures of fatty acids, dicarboxylic acids and sorbitol, and the subsequent quaternisation and/or ethoxylation of the esters obtained.

In our Spanish patent application no. P-200000697, which is awaiting publication, a description is given of novel aqueous textile-softening compositions containing cationic surfactants and esterquats of alkanolamine esters based on the esterification reaction of optionally alkoxylated alkanolamines, dicarboxylic acids, and optionally alkoxylated fatty alcohols and, optionally, fatty acids. Furthermore, the mentioned patent application describes the optional possibility of including in the softening compositions to which it relates, up to a maximum of 40% of non-ionic surfactants of softening character, expressed relative to the total weight of softening agent, and other softening cationic active substances. That patent application describes compositions in which the active softening substance is formed predominantly by cationic surfactants.

Also well known is the great interest, existing in the field of fibre-softeners and fibre-conditioners, in the total or partial substitution, in the softening compositions, of the cationic agents by non-ionic agents, given that the last-mentioned agents exhibit better behaviour from an ecotoxicological and environmental point of view. Special consideration has been given to non-ionic agents of the ester type, given their higher degree of biodegradability and lower degree of toxicity.

However, it is also well known that compositions based on the mentioned non-ionic components are deficient in terms of softening power when compared with conventional softening formulations. This matter is dealt with in at least the following patents and patent applications: U.S. Pat. No. 5,447,643, U.S. Pat. No. 5,854,201, EP-A-0893490, U.S. Pat. No. 5,593,614, U.S. Pat. No. 4,179,382, U.S. Pat. No. 4,237,016 and WO-A-9812293.

As far as the authors of the present invention know, no formulation based predominantly on non-ionic surfactants has been obtained which offers properties similar to those of conventional formulations based principally on cationic surfactants.

SUMMARY OF THE INVENTION

The subject-matter of the present invention is the use of cationic surfactants and/or esterquats of esters obtained by the esterification reaction of alkanolamines with dicarboxylic acids and fatty alcohols, described in Spanish patent application no. P200000697, as auxiliaries which improve the softening and conditioning efficiency in respect of natural and synthetic fibres of surfactants of non-ionic character, especially those containing functional groups of the ester type.

The subject-matter of the present invention also includes aqueous softening compositions for textile fibres, which compositions contain, as the softening active substance, non-ionic surfactants principally containing optionally alkoxylated ester groups and, as auxiliaries reinforcing the softening effect, the cationic surfactants or esterquats mentioned above.

DESCRIPTION OF THE INVENTION

The authors of the present invention have surprisingly found that, although used in a minor proportion, the cationic surfactants and/or esterquats obtained from alkanolamine esters with dicarboxylic acids and fatty alcohols, described in Spanish patent application no. P200000697, substantially improve the fibre-softening and fibre-conditioning efficiency of compositions containing more than 40% by weight of non-ionic surfactants based on the total weight of active softening substance. The mentioned compounds also facilitate ironing in the case of textile fibres and combing in the case of natural fibres.

Although the present invention should not be regarded as bound to the theory discussed hereinafter, it is believed that those beneficial effects may be attributable to the fact that the mentioned cationic surfactants or esterquats promote the deposition of surfactants of non-ionic character on natural and synthetic fibres.

Therefore, the mentioned compounds can be used, as auxiliaries that improve the softening and conditioning efficiency of non-ionic surfactants, to manufacture fibre-softening and fibre-conditioning compositions that are based principally on non-ionic surfactants, or on mixtures of non-ionic surfactants and cationic surfactants, and in which the percentage of non-ionic surfactant is higher than 40% of the total weight of the active softening substance. Their use in compositions for softening textiles, in addition to improving the feel of the fabric, facilitates ironing and reduces the appearance of creases during washing, and their use in hair-conditioning compositions or as shampoo additives improves ease of combing and the appearance of the hair.

The present invention also includes aqueous softening compositions for textiles or other synthetic or natural fibres, which compositions contain:

(a) cationic surfactants or esterquats obtainable from alkanolamine esters with dicarboxylic acids and fatty alcohols, (b) optionally one or more cationic surfactants acting as softeners or conditioners for textiles or other fibres, and (c) one or more non-ionic surfactants that condition textiles or other fibres, in which the sum of components (a), (b) and (c) is from 2% to 60% by weight, so that, relative to the total amount of components (a), (b) and (c), (i) the proportion by weight of component (a) is from 5% to 60%, (ii) the proportion by weight of component (b) is from 0% to 30% and (iii) the proportion by weight of component (c) is from 40% to 95%, the remainder of the components being water and other optional components selected from those customarily used in aqueous softening compositions for textiles.

Preferably, the aqueous textile-softening compositions to which the invention relates contain from 3% to 50% by weight of the sum of components (a), (b) and (c), so that, relative to the total amount of components (a), (b) and (c), (i) the proportion by weight of component (a) is from 20% to 60%, (ii) the proportion by weight of component (b) is from 0% to 20% and (iii) the proportion by weight of component (c) is from 40% to 80%, the remainder of the components being water and other optional components selected from those customarily used in aqueous softening compositions for textiles.

Cationic Surfactants and Esterquats of Alkanolamine Esters

The alkanolamine esters used in the present invention are those obtainable by the esterification reaction of an alkanolamine of the general formula (I)

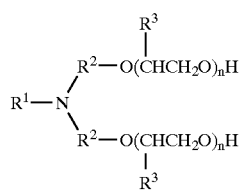
(I)

with a dicarboxylic acid, or with a reactive derivative thereof, of the general formula (II)

(II)

and with an optionally alkoxylated fatty alcohol of the general formula (III)

(III)

in which formulae $R^1$ is hydrogen, a $C_1$–$C_6$ alkyl group or the residue

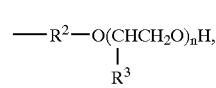

$R^2$ is a $C_1$–$C_6$ alkylene group, $R^3$ is hydrogen or methyl, n is 0 or an integer from 1 to 20, $R^4$ is an optionally substituted or unsaturated $C_1$–$C_{36}$ alkylene group, or arylene, and $R^5$ is a linear or branched $C_2$–$C_{22}$ alkyl or alkenyl group.

It is optionally also possible to incorporate in the reaction mixture a fatty acid of the general formula (IV)

(IV), in which $R^6$ is a linear or branched $C_6$–$C_{23}$ alkyl or alkenyl group, or an alkyl ester or a glyceride of the fatty acid and/or an optionally alkoxylated polyol.

The following may be mentioned as examples of alkanolamines that may be used: triethanolamine, N-methyldiethanolamine, N-methyldiisopropanolamine and triisopropanolamine, each of which is optionally alkoxylated with ethylene oxide or propylene oxide, or mixtures thereof, non-alkoxylated alkanolamines, especially triethanolamine, being preferred.

There may be mentioned as examples of dicarboxylic acids, although this is not intended to be an exhaustive list, succinic, malic, glutaric, adipic, sebacic, pimelic, suberic, maleic and terephthalic acid, and also those known as dimers of fatty acids or dimeric fatty acids which are obtained by thermal oligomerisation of unsaturated fatty acids, such as those marketed by Unichema International under the name PRIPOL®, for example PRIPOL® 1009, or mixtures of those acids. Adipic acid is preferred.

The fatty alcohols of formula (III), which are optionally alkoxylated with ethylene oxide or propylene oxide, may be those which are obtained from fats and oils of natural origin, for example from tallow, palm, olive, coconut, sunflower, soya, grape marc, rape, etc., hydrogenated or non-hydrogenated, preference being given to non-alkoxylated alcohols containing predominantly from 16 to 18 carbon atoms.

Examples of fatty acids which may optionally be included in the esterification reaction are those which are obtained from vegetable and animal oils and fats, such as coconut, tallow, palm, sunflower, soya, olein, grape marc, rape, etc., and which are optionally totally or partially hydrogenated, and also purified or synthetic fatty acids, such as lauric acid, stearic acid, palmitic acid, oleic acid, linoleic acid, 2-ethylhexanoic acid, etc.

The polyols which may also optionally be included in the esterification reaction may be, for example, glycerol, pentaerythritol, sucrose, glucose, sorbitol or glycols, such as ethylene glycol, propylene glycol, diethylene glycol, dipropylene glycol, etc.

For the purposes of the present invention, it is advantageous that:
- the molar ratio of the dicarboxylic acid to the alkanolamine is from 0.2 to 1.2, preferably from 0.3 to 0.9, more preferably from 0.4 to 0.8,
- the molar ratio of the sum of the fatty alcohol and the fatty acid to the alkanolamine is from 0.2 to 2.0, and
- the molar ratio of the fatty acid to the fatty alcohol is from 0 to 10, preferably from 0.1 to 5.0, more preferably from 0.5 to 1.0.

The esterification reaction is carried out by methods known per se, such as those already described in Spanish patent application no. P-200000697 which is incorporated herein by reference.

Preferably, the esterification reaction is effected by condensing the dicarboxylic acid, and optionally the fatty acid, with a mixture of the alkanolamine and the fatty alcohol, and optionally the polyol, at a temperature of from 120° C. to 220° C. for a period of from 2 to 10 hours, preferably at a reduced pressure of some 5 to 200 mbar and in the presence of any of the catalysts already known for the esterification of conventional esterquats, for example hypophosphorous acid or paratoluenesulphonic acid, and also in the presence of any of the usual stabilisers and anti-oxidants, such as tocopherols, BHT, BHA, citric acid, etc. The esterification reaction can also be effected by first condensing the dicarboxylic acid with the triethanolamine, then adding the fatty alcohol.

It will be apparent to the person skilled in the art that the esterification reaction can alternatively be carried out by other conventional techniques, starting from reactive derivatives of dicarboxylic acids, for example their acid chlorides, esters or anhydrides.

The esters so obtained are used to prepare the cationic surfactants and esterquats whose use in softening compositions based on non-ionic surfactants forms part of the subject-matter of the present invention. The cationic surfactants may be the esterquats obtainable on the basis of their quaternisation with alkylating agents, or the addition salts of alkanolamine esters with mineral or organic acids, such as hydrochloric acid, sulphuric acid, phosphoric acid, citric acid, lactic acid, etc. Esterquats are preferred as fibre-softening cationic surfactants.

Those esterquats are obtained from the alkanolamine esters of the invention by means of an additional quaternisation reaction, which is likewise known per se, such as, for example, described in the patent application WO-A-9849132 mentioned above.

For example, the reaction mixture resulting from esterification is reacted with alkylating products, such as methyl chloride, methyl bromide, dimethyl sulphate, diethyl sulphate, dimethyl carbonate, etc., preferably in the presence of organic solvents which facilitate its manageability, such as isopropanol, ethanol, propylene glycol, ethylene glycol, dipropylene glycol, fatty alcohols, etc., and then the pH is adjusted to from 1.5 to 7.0, preferably from 2 to 4.5, by the addition of an acid, such as any of hydrochloric acid, sulphuric acid, phosphoric acid, citric acid, etc.

Optional Cationic Surfactants

Cationic surfactants that act as textile-softeners and that may constitute component (b) of the softening compositions of the invention are well known by the expert.

Among these, mention may be made of quaternary ammonium compounds whose hydrophobic chains are not interrupted by an ester group, for example those described in patents U.S. Pat. No. 4,719,382 and U.S. Pat. No. 4,237,016, of which the most well known is hydrogenated tallow dialkyldimethylammonium chloride, also known as DTDMAC, such as that marketed by KAO Corporation, S.A. under the mark QUARTAMIN® D86P.

However, the esterquats, whose descriptions can be found, among many others, in the documents already mentioned in this description, which are incorporated herein by reference, and of which the following esterquats may be mentioned as important examples, are preferred:
- the quaternised diesters of fatty acids with 1,2-dihydroxy-3-dimethylaminopropane, such as described by U.S. Pat. No. 4,137,180 and European patent application EP-A-0585040,
- the quaternised diesters of fatty acids with N-methyldiethanolamine, such as those described in French patent application FR-A-1593921 and in European patent EP-B-0239910, for example the hydrogenated tallow diester quaternised with methyl chloride and marketed by KAO Corporation, S.A. under the mark KAOSOFT® PH,
- the amido ester salts of fatty acids with N-methyl-N-aminopropylethanolamine, for example that marketed by KAO Corporation under the mark KAOSOFT® 1,
- the quaternised diesters of fatty acids with triethanolamine, such as those described in U.S. Pat. No. 3,915,867 and in a large number of later patents, for example the diesters of partially hydrogenated tallow which are quaternised with dimethyl sulphate and which are marketed by KAO Corporation, S.A. under the marks TETRANYL® AT-7590 and TETRANYL® L1/90.

It should be pointed out that when reference is made to the term "diester" this is intended to indicate that the diester predominates in the mixture, although the product may always contain variable amounts of monoester compounds and, in the case of triethanolamine, triester compounds.

There also come into consideration as cationic surfactants having a softening character, the oligomeric cationic surfactants described in patent application WO-A-9849132, for example those marketed by KAO Corporation, S.A. under the references TETRANYL® PH-2 and TETRANYL® PH-5.

Non-Ionic Conditioning Surfactants

The non-ionic surfactants that condition textiles or other fibres and that constitute component (c), which predominates in the formula, are also well known to the person skilled in the art and of these there may be mentioned: fatty acids and their esters, especially those containing from 8 to 18 carbon atoms, which are linear or branched and alkoxylated or non-alkoxylated; alkoxylated or non-alkoxylated Guerbet alcohols; esters of glycerol and polyglycerol, for example HOSTACERIN DGMS and HOSTACERIN DGI marketed by Clariant; xylitol esters; alkoxylated or non-alkoxylated sorbitan esters, for example KAOPAN marketed by KAO Corporation, S.A.; esters of sugars, such as glucose, fructose, galactose, mannose, xylose, arabinose, ribose, 2-deoxyribose and sucrose; $C_{8-18}$ fatty alcohols; optionally alkoxylated glycerol esters, for example LEVENOL marketed by KAO Corporation, S.A.; ethoxylated polyglycerol esters, for example HOSTACERIN DGL and HOSTACERIN DGSB marketed by Clariant; alkyl polyglucosides, for example AG-10LK, marketed by Kao Japan; and alkoxylated or non-alkoxylated pentaerythritol esters, for example RADIA 7171 and RADIA 7176, marketed by Oleofina. Also exhibiting a good conditioning power are non-ionic surfactants with amide groups, among which there may be mentioned derivatives of amine, such as glucamine, for example MEDIALAN GAC and MEDIALAN GAL marketed by Clariant, and also derivatives of methylethanolamine, diethanolamine, isopropanolamine and monoethanolamine, with linear or branched fatty acids, especially $C_{8-18}$ fatty acids.

Other non-ionic compounds which may be used as textile-conditioners are waxes, such as paraffins, microcrystalline waxes derived from petroleum, and synthetic waxes.

Of all the non-ionic surfactants described, the following are especially preferred: glycerol esters that are ethoxylated, sorbitan monoesters and pentaerythritol esters, especially those having a tallow, hydrogenated tallow, palm, behenic or oleic chain.

Other Optional Components

In referring to other optional components, without this having to be regarded as an exhaustive description of all possibilities, which, on the other hand, are well known to the person skilled in the art, the following may be mentioned:

a) other products that enhance the performance of the softening compositions, such as silicones, amine oxides, anionic surfactants, such as lauryl ether sulphate or lauryl sulphate, amphoteric surfactants, such as cocoamidopropyl betaine or alkyl betaines, sulphosuccinates, polyglucoside derivatives, etc.

b) stabilising products, such as salts of amines having a short chain, which are quaternised or non-quaternised, for example of triethanolamine, N-methyldiethanolamine, etc., and also non-ionic surfactants, such as ethoxylated fatty alcohols, ethoxylated fatty amines, ethoxylated alkyl phenols, etc.

c) products that improve viscosity control, for example inorganic salts, such as calcium chloride, magnesium chloride, calcium sulphate, sodium chloride, etc.; products which can be used to reduce viscosity in concentrated compositions, such as compounds of the glycol type, such as, for example, ethylene glycol, dipropylene glycol, polyglycols, etc.; and thickening agents for diluted compositions, for example, polymers derived from cellulose, guar gum, etc.

d) components for adjusting the pH, which is preferably from 1.5 to 4.5, such as any type of inorganic and/or organic acid, for example hydrochloric, sulphuric, phosphoric, citric acid etc.

e) agents that improve soil release, such as the known polymers or copolymers based on terephthalates.

f) Bactericidal preservative agents, such as formol, Kathon GC, Bronopol, etc.

g) Other products such as antioxidants, colouring agents, perfumes, germicides, fungicides, anti-corrosive agents, anti-crease agents, opacifiers, optical brighteners, pearl lustre agents, etc.

The softening compositions can be obtained by simply mixing their components until they have been dispersed or dissolved, using methods well known by the person skilled in the art.

The following Examples are given in order to provide the person skilled in the art with a sufficiently clear and complete explanation of the present invention but are not to be regarded as limiting the basic aspects of the subject-matter thereof, as have been explained in the earlier portions of this description.

EXAMPLES

Examples 1 to 5

Preparation of the Alkanolamine Esters

The products of Table 1 are prepared by using the reagents in the amounts indicated in Table 1, in accordance with the following general esterification method:

The alkanolamine and the fatty alcohol and, if appropriate, the polyol are mixed in a reaction flask equipped with an agitator, a temperature probe and an inlet for an inert gas. There are added as esterification catalysts: 50% by weight hypophosphorous acid in an amount sufficient to obtain 1000 ppm based on the total charge or, alternatively, paratoluenesulphonic acid in an amount sufficient to obtain 500 ppm based on the total charge. The mixture is heated in an inert atmosphere to 100° C., the dicarboxylic acid is added and, if appropriate, the fatty acid, the temperature rising to 170° C., and that temperature is maintained while the water of esterification is distilled, until the acidity index of the mixture is below 5 mg KOH/g.

If appropriate, the esterification product is subjected to a conventional ethoxylation reaction with ethylene oxide.

TABLE 1

Reagents used in the esterification reaction

| Ex. | Amine | Dicarboxy-lic acid | Fatty alcohol | Fatty acid |
|---|---|---|---|---|
| 1 | TEA (1 mol) | Adipic (0.5 mol) | Hydrogenated tallow (0.6 mol) | — |
| 2 | TEA (1 mol) | Adipic (0.7 mol) | Hydrogenated tallow (1.2 mol) | — |
| 3 | TEA (1 mol) | Adipic (0.8 mol) | Hydrogenated tallow (0.2 mol) | Tallow (0.6 mol) |
| 4 | TEA (1 mol) | Adipic (0.5 mol) | Hydrogenated tallow (0.2 mol) | Tallow (0.5 mol) |
| 5 | MDEA (1 mol) | Adipic (0.4 mol) | Hydrogenated tallow (0.5 mol) | Tallow (0.6 mol |

TEA: triethanolamine; MDEA: methyldiethanolamine

The product obtained in the esterification reaction, which constitutes the subject-matter of the invention, is a very complex mixture of chemical compounds, and in the crude form in which it is obtained it is useful in the preparation of cationic surfactants and esterquats which can be used for the purpose of the invention.

Examples 6 to 10

Preparation of the Esterquats

The esterquats of Table 2 are prepared by using the reagents indicated in Table 2, in accordance with the following general quaternisation methods:

Quaternisation with methyl chloride—The product resulting from the esterification stage, together with a sufficient amount of isopropyl alcohol for said alcohol to represent from approximately 8% to approximately 12% by weight relative to the crude quaternised product, and optionally BHT in the amount necessary to obtain 500 ppm based on the total charge, is introduced into a reaction flask which is capable of operating under conditions of pressure and which is equipped with an agitator, a charging funnel and a temperature probe. The mixture is heated to 85°–90° C. and an amount of methyl chloride slightly higher than the stoichiometric amount is added, with the pressure being maintained at from 2 to 3 kg/cm². When the addition of methyl chloride is complete, the reaction mixture is maintained under agitation at 80°–85° C. for 1–2 hours.

Quaternisation with dimethyl sulphate—The product resulting from the esterification stage, together with a sufficient amount of isopropyl and/or ethyl alcohol to represent from approximately 8% to approximately 12% by weight relative to the end product and, optionally, BHT in an amount sufficient to obtain 500 ppm based on the total charge, is introduced into a 1-litre reaction flask equipped with an agitator, a temperature probe and a charging funnel.

The mixture is heated to 50° C. and an amount of dimethyl sulphate slightly lower than the stoichiometric amount is added slowly over a period of 1–2 hours. Once the addition is complete, the reaction mixture is maintained at 50°–55° C. for 3 to 4 more hours.

TABLE 2

Reagents used in the quaternisation reaction

| Example | Alkanolamine ester | Alkylating agent |
| --- | --- | --- |
| 6 | That obtained in Example 1 | Dimethyl sulphate |
| 7 | That obtained in Example 2 | Methyl chloride |
| 8 | That obtained in Example 3 | Dimethyl sulphate |
| 9 | That obtained in Example 4 | Dimethyl sulphate |
| 10 | That obtained in Example 5 | Dimethyl sulphate |

The esterquats so obtained are also a very complex mixture of chemical compounds and in the crude form in which they are obtained they are useful in the preparation of compositions for softening and conditioning natural and synthetic fibres.

Example 11

Comparison of the Softness on Textiles of Non-Ionic Surfactants and Conventional Cationic Surfactants The comparative softness tests with non-ionic surfactants and conventional cationic surfactants are carried out under conditions similar to those occurring in real use, by comparing the, results obtained at doses corresponding to two ratios of softening active substance to weight of textile fibre: 0.1% and 0.2% dry weight of softening active substance relative to the weight of the fabric.

The tests are effected on cotton towels, carrying out five washes and five softening operations in the rinsing stage, one after each wash, using water of 25° HF (French degrees of hardness), in a washing machine of the MIELE brand and using the detergent marketed in Spain under the mark COLON by the company Benckiser.

The results are evaluated by calculating the statistical mean of the values obtained on the basis of the quantification of the subjective opinion of 20 experienced panellists who use as references: a) a control, which is awarded the value 0, comprising a cotton towel which is not treated with a softener after its washes; and b) a reference value which is assigned the value 10 and which corresponds to the softness result obtained with the product QUARTAMIN D86P marketed by KAO Corporation, S.A. which is hydrogenated tallow dialkyldimethylammonium chloride, a conventional softening quaternary compound recognized to be highly effective, although with a lesser degree of ecological tolerance owing to the fact that it does not have ester groups intercalated in its hydrophobic chains. The results obtained are shown in Table 3.

TABLE 3

Comparative softness tests on textiles

| Active softening substance | Softness |
| --- | --- |
| Pentaerythritol tetrastearate | 4 |
| AG-10 LK | 4 |
| KAOPAN B-10 | 5 |
| LEVENOL TH-224 | 3 |

TABLE 3-continued

Comparative softness tests on textiles

| Active softening substance | Softness |
| --- | --- |
| MEDIALAN GAC | 5 |
| QUARTAMIN D86P (comparative reference) | 10 |
| TETRANYL AT-7590 | 7 |

AG-10 LK is an alkyl polyglucoside marketed by KAO Japan.
KAOPAN B-10 is a sorbitan ester marketed by KAO Corporation, S.A.
LEVENOL TH-224 is an alkoxylated glycerol ester marketed by KAO Corporation, S.A.
MEDIALAN GAC is a glucamine derivative marketed by Clariant.
TETRANYL AT-7590 is a conventional esterquat derived from triethanolamine and marketed by KAO Corporation, S.A.□

The results set out in Table 3 clearly show that the non-ionic surfactants have a deficient softening power compared with that of conventional cationic surfactants which can perhaps be attributed to the poor absorption thereof on the fibre.

Examples 12 to 24

Aqueous Textile-Softening Compositions

Conventional agitating and mixing methods are used to prepare the softening compositions shown in Table 4, in which the percentages indicated are based on the total weight of the composition. The softening efficiency of the compositions is evaluated in accordance with the method described in Example 11.

In Table 4:

| | |
| --- | --- |
| TETRANYL AT-7590 | is a conventional esterquat derived from triethanolamine and marketed by KAO Corporation, S.A. |
| MEDIALAN GAC | is a glucamine derivative marketed by Clariant |
| TETRANYL Ll-90 | is a conventional esterquat derived from triethanolamine and marketed by KAO Corporation, S.A. |
| KAOSOFT PH | is a conventional esterquat derived from methyldiethanolamine and marketed by KAO Corporation, S.A. |
| KAOPAN SP-120 | is a sorbitan ester having a stearic chain and marketed by KAO Corporation, S.A. |
| KAOPAN O-120 | is a sorbitan ester having an oleic chain and marketed by KAO Corporation, S.A. |
| KAOPAN B-120 | is a sorbitan ester having a behenic chain and marketed by KAO Corporation, S.A. |
| LEVENOL TH-224 | is an ethoxylated glycerol ester having a hydrogenated tallow chain and marketed by KAO Corporation, S.A. |

TABLE 4

Aqueous textile-softening compositions and their softening efficiency□

| Ex. | Cationic surfactant A | Non-ionic surfactant | $MgCl_2$ | Minority components[B] and water | Softness |
| --- | --- | --- | --- | --- | --- |
| 12 | Esterquat example 6 (2.9%) | MEDIALAN GAC (2.1%) | — | up to 100% | 9 |

TABLE 4-continued

Aqueous textile-softening compositions and their softening efficiency[A]

| Ex. | Cationic surfactant A | Non-ionic surfactant | MgCl$_2$ | Minority components[B] and water | Softness |
|---|---|---|---|---|---|
| 13 | Esterquat example 6 (5.0%) | — | — | up to 100% | 9 |
| 14 | Esterquat example 7 (1.5%) | Pentaerythritol tetrastearate (3.5%) | — | up to 100% | 8 |
| 15 | Esterquat example 7 (5.0%) | — | — | up to 100% | 8 |
| 16 | Esterquat example 8 (1.5%) | KAOPAN O-120 (3.5%) | — | up to 100% | 8 |
| 17 | Esterquat example 9 (3.0%) KAOSOFT PH (0.5%) | LEVENOL TH-224 (11.5%) | 0.16% | up to 100% | 10 |
| 18 | Esterquat example 9 (1.0%) | LEVENOL TH-224 (4.0%) | — | up to 100% | 9 |
| 19 | Esterquat example 6 (1.5%) TETRANYL AT-7590 (0.5%) | KAOPAN SP-120 (3%) | — | up to 100% | 9 |
| 20 | Esterquat example 10 (2%) | KAOPAN SP-120 (3%) | — | up to 100% | 9 |
| 21 | Esterquat example 10 (1%) | KAOPAN SP-120 (4%) | — | up to 100% | 8 |
| 22 | Esterquat example 6 (1.9%) TETRANYL AT-7590 (1.0%) | Pentaerythritol tetrastearate (2.1%) | — | up to 100% | 9 |
| 23 | Esterquat example 10 (3.0%) TETRANYL L1/90 (3.0%) | Pentaerythritol tetrastearate (9%) | — | up to 100% | 9 |
| 24 | Esterquat example 7 (2.9%) | KAOPAN B-120 (2.1%) | — | up to 100% | 10 |

[A]Dry active substance relative to the total weight of the composition
[B]Perfumes, colouring agents, preservatives, etc.

The softness results given in Table 4 show that all of the compositions that contain non-ionic surfactants exhibit a high degree of softening efficiency despite those surfactants being present in a high proportion of more than 40% by weight based on the total weight of the softening active substance.

This shows, by comparison with the results given in Table 3, that the use of cationic surfactants derived from alkanolamine esters with dicarboxylic acids and fatty alcohols, as additives mixed into softening compositions based on non-ionic surfactants, notably improves the softening efficiency of those softening compositions.

It should be emphasised, as may be observed by comparing the results of Examples 12 and 13, on the one hand, and 14 and 15, on the other hand, that the selection of the type of cationic surfactant which contributes to the object of the present invention enables a very large portion thereof to be replaced by the non-ionic surfactant, without thereby losing softening efficiency.

What is claimed is:

1. A method of softening and conditioning natural and synthetic fibers with compositions that include more than 40% by weight of fiber conditioning non-ionic surfactants, based on the total weight of softening active substances, which comprises introducing into said fibers a cationic surfactant obtainable by the formation of addition salt of an alkanolamine ester with a mineral organic acid or by quaternization of an alkanolamine ester by reaction with an alkylating agent, said alkanolamine ester prepared by the esterification reaction of an alkanolamine of the general formula (I)

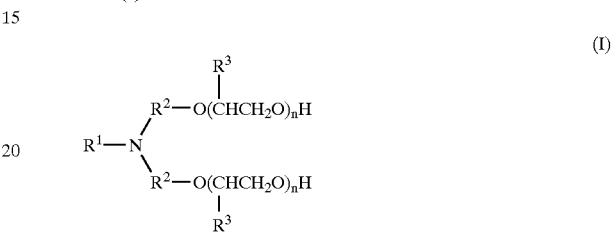
(I)

with a dicarboxylic acid, or with a reactive derivative thereof, of the general formula (II)

$$HOOC-R^4-COOH \qquad (II)$$

with an optionally alkoxylated fatty alcohol of the general formula (III)

(III)

in which formulae $R^1$ is hydrogen, a $C_1$–$C_6$ alkyl group or the residue

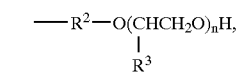

$R^2$ is a $C_1$–$C_6$ alkylene group, $R^3$ is hydrogen or methyl, n is 0 or an integer from 1 to 20, $R^4$ is an optionally substituted or unsaturated $C_1$–$C_{36}$ alkylene group, or arylene, and $R^5$ is a linear or branched $C_2$–$C_{22}$ alkyl or alkenyl group
and with a fatty acid of the general formula (IV)

$$R^6-COOH \qquad (IV),$$

in which $R^6$ is a linear or branched $C_6$–$C_{23}$ alkyl or alkenyl group, or an alkyl ester or a glyceride of the fatty acid, and/or an optionally alkoxylated polyol is incorporated into the esterification.

2. A method according to claim 1, wherein the alkanolamine of formula (I) is selected from triethanolamine, N-methyldiethanolamine, N-methyldiisopropanolamine and triisopropanolamine, each of which is optionally alkoxylated with ethylene oxide, propylene oxide, or mixtures thereof.

3. A method according to claim 1, wherein the dicarboxylic acid of formula (II) is selected from the group consisting of succinic acid, malic acid, glutaric acid, adipic acid, sebacic acid, pimelic acid, suberic acid, maleic acid, terephthalic acid, the thermal oligomerization product of one or more unsaturated fatty acids, and mixtures thereof.

4. A method according to claim 1, wherein the fatty alcohol of formula (III) obtained from fats and oils is of natural origin are optionally hydrogenated and/or alkoxylated.

5. A method according to claim 4, wherein the fatty alcohol of formula (III) is an alcohol obtained from tallow, palm, olive, coconut, sunflower, soya, grape marc or rape, and is hydrogenated or non-hydrogenated and is optionally alkoxylated with ethylene oxide or propylene oxide.

6. A method according to claim 1, wherein the molar ratio of the dicarboxylic acid to the alkanolamine is from 0.2 to 1.2; the molar ratio of the sum of the fatty alcohol and the fatty acid to the alkanolamine is from 0.2 to 2.0; and the molar ratio of the fatty acid to the fatty alcohol is from 0 to 10.

7. A method according to claim 6, wherein the molar ratio of the dicarboxylic acid to the alkanolamine is from 0.3 to 0.9.

8. A method according to claim 7, wherein the molar ratio is from 0.4 to 0.8.

9. A method according to claim 6, wherein the molar ratio of the fatty acid to the fatty alcohol is from 0.1 to 5.0.

10. A method according to claim 6, wherein the molar ratio of the fatty acid to the fatty alcohol is from 0.5 to 1.0.

11. A method according to claim 1, wherein the mineral organic acid is selected from the group consisting of hydrochloric, sulphuric, phosphoric, citric and lactic acid.

12. A method according to claim 1, wherein the alkylating agent is selected from the group consisting of methyl chloride, methyl bromide, dimethyl sulphate, diethyl sulphate and dimethyl carbonate.

13. A method according to claim 1, wherein the fibre-conditioning non-ionic surfactant is selected from the group consisting of fatty acids, linear or branched, alkoxylated or non-alkoxylated esters of fatty acids, containing from 8 to 18 carbon atoms, alkoxylated or non-alkoxylated Guerbet alcohols, optionally alkoxylated glycerol and polyglycerol esters, xylitol esters, alkoxylated or non-alkoxylated sorbitan esters, esters of sugars selected from the group consisting of glucose, fructose, galactose, mannose, xylose, arabinose, ribose, 2-deoxyribose and sucrose, $C_{8-18}$ fatty alcohols, alkyl polyglucosides, non-ionic surfactants with amide groups derived from amines selected from the group, consisting of glucamine, and derivatives of methylethanolamine, diethanolamine, isopropanolamine or monoethanolamine, with linear or branched fatty acids especially those containing from 8 to 18 carbon atoms, waxes selected from the group consisting of paraffins, microcrystalline waxes derived from petroleum, and synthetic waxes, and pentaerythritol esters, having a chain selected from the group consisting of tallow, hydrogenated tallow, palm, behenic and oleic.

14. A method according to claim 13, wherein the fiber-conditioning non-ionic surfactant is an ethoxylated, sorbitan monoester, glycerin ester or a pentaerythritol ester, having a tallow, hydrogenated tallow, palm, behenic or oleic chain.

15. An aqueous softening composition for textiles or other synthetic or natural fibers, which comprises:
  (a) the cationic surfactant defined in claim 1;
  (b) optionally one or more cationic surfactants acting as softeners or conditioners for textiles or other fibers; and
  (c) one or more non-ionic surfactants that condition textiles or other fibres, in which the sum of components (a), (b) and (c) is from 2% to 60% by weight, and relative to the total amount of components (a), (b) and (c),
    (i) the proportion by weight of component (a) is from 5% to 60%,
    (ii) the proportion by weight of component (b) is from 0% to 30% and
    (iii) the proportion by weight of component (c) is from 40% to 95%.

16. A composition according to claim 15, wherein the sum of (a), (b) and (c) is from 3% to 50% by weight, and relative to the total amount of components (a), (b) and (c),
  (i) the proportion by weight of component (a) is from 20% 60%,
  (ii) the proportion by weight of component (b) is from 0% to 20% and
  (iii) the proportion by weight of component (c) is from 40% to 80%.

17. A composition according to claim 16, wherein the non-ionic surfactant conditioning textiles and other fibers is selected from the group consisting of fatty acids, linear or branched, alkoxylated or non-alkoxylated esters of fatty acids, containing from 8 to 18 carbon atoms, alkoxylated or non-alkoxylated Guerbet alcohols, optionally alkoxylated glycerol and polyglycerol esters, xylitol esters, alkoxylated or non-alkoxylated sorbitan esters, esters of sugars selected from the group consisting of glucose, fructose, galactose, mannose, xylose, arabinose, ribose, 2-deoxyribose and sucrose, $C_{8-18}$ fatty alcohols, alkyl polyglucosides, non-ionic surfactants with amide groups derived from amines selected from the group consisting of glucamine, and derivatives of methylethanolamine, diethanolamine, isopropanolamine or monoethanolamine, with linear or branched fatty acids especially those containing from 8 to 18 carbon atoms, waxes selected from the group consisting of paraffins, microcrystalline waxes derived from petroleum, and synthetic waxes, and pentaerythritol esters, having a chain selected from the group consisting of tallow, hydrogenated tallow, palm, behenic and oleic.

18. A composition according to claim 15, wherein the non-ionic surfactant conditioning textiles or other fibers is selected from the group consisting of fatty acids, linear or branched, alkoxylated or non-alkoxylated esters of fatty acids, containing from 8 to 18 carbon atoms, alkoxylated or non-alkoxylated Guerbet alcohols, optionally alkoxylated glycerol and polyglycerol esters, xylitol esters, alkoxylated or non-alkoxylated sorbitan esters, esters of sugars selected from the group consisting of glucose, fructose, galactose, mannose, xylose, arabinose, ribose, 2-deoxyribose and sucrose, $C_{8-18}$ fatty alcohols, alkyl polyglucosides, non-ionic surfactants with amide groups derived from amines selected from the group consisting of glucamine, and derivatives of methylethanolamine, diethanolamine, isopropanolamine or monoethanolamine, with linear or branched fatty acids especially those containing from 8 to 18 carbon atoms, waxes selected from the group consisting of paraffins, microcrystalline waxes derived from petroleum, and synthetic waxes, and pentaerythritol esters, having a chain selected from the group consisting of tallow, hydrogenated tallow, palm, behenic and oleic.

* * * * *